US006598974B2

(12) United States Patent
Jones et al.

(10) Patent No.: US 6,598,974 B2
(45) Date of Patent: Jul. 29, 2003

(54) METHOD AND APPARATUS FOR MEASURING WAVEFRONT ABERRATIONS

(75) Inventors: Larry G. Jones, Jacksonville, FL (US); Denwood Ross, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 10 days.

(21) Appl. No.: 09/850,942

(22) Filed: May 8, 2001

(65) Prior Publication Data

US 2002/0167642 A1 Nov. 14, 2002

(51) Int. Cl.⁷ ................................................ A61B 3/10
(52) U.S. Cl. ...................................................... 351/221
(58) Field of Search ................................. 351/200, 205, 351/215, 221, 246, 213; 359/483; 356/364, 601

(56) References Cited

U.S. PATENT DOCUMENTS

| 5,303,709 | A | * | 4/1994 | Dreher et al. | 351/221 |
| 5,787,890 | A | * | 8/1998 | Reiter et al. | 351/215 |
| 5,949,521 | A | * | 9/1999 | Williams et al. | 351/246 |
| 6,095,651 | A | * | 8/2000 | Williams et al. | 351/246 |
| 6,112,114 | A | * | 8/2000 | Dreher | 351/215 |
| 6,270,221 | B1 | * | 8/2001 | Liang et al. | 351/221 |
| 6,361,170 | B1 | * | 3/2002 | Bille | 351/221 |

FOREIGN PATENT DOCUMENTS

| EP | 172133 A1 | 2/1986 |
| EP | 172133 B1 | 12/1987 |

OTHER PUBLICATIONS

Taiwan Telphone Book(Manufacturers) vol. C99, Spring 2000, p. 1692.
Eight photograph sheets of Lifestyle Frequency Progressive Package, The Lifestyle Company, Inc, Morganville, New Jersey 07751.

\* cited by examiner

Primary Examiner—Marvin M. Lateef
Assistant Examiner—John R. Sanders

(57) ABSTRACT

An apparatus and method for measuring wavefront aberrations. A beam splitter separates the aberrated wavefront into two components, mirror arrays focus each of the components to a plurality of discrete lines with the discrete lines of one component having a different orientation than the discrete lines of the other component, and an imaging device detects the discrete lines to determine wavefront aberrations. The method includes separating the wavefront into two components, focusing each of the components into a plurality of discrete lines with the discrete lines of one component having a different orientation than the discrete lines of the other component, and detecting information related to the discrete lines.

24 Claims, 4 Drawing Sheets

METHOD AND APPARATUS FOR MEASURING WAVEFRONT ABERRATIONS

FIELD OF THE INVENTION

The present invention relates generally to optical instruments and, more particularly, to a method and apparatus for measuring wavefront aberrations. The present invention is particularly useful, but not exclusively so, for measuring the optical wavefront in ophthalmic applications, e.g., measurement of aberrations of the eye, developing corrective devices such as lenses (e.g., contact, spectacle, and intraocular), and for evaluating the ocular aberrations before, during and after refractive surgery to improve vision.

BACKGROUND OF THE INVENTION

The human eye is an optical system employing several lens elements to focus light rays representing images onto the retina within the eye. The sharpness of the images produced on the retina is a factor in determining the visual acuity of the eye. Imperfections within the lens and other components and material within the eye, however, may cause the light rays to deviate from a desired path. These deviations, referred to as aberrations, result in blurred images and decreased visual acuity. Hence, a method and apparatus for measuring aberrations is desirable to aid in the correction of such problems.

One method of detecting aberrations introduced by an eye involves determining the aberrations of light rays exiting from within the eye. A beam of light directed into the eye as a point on the retina is reflected or scattered back out of the eye as a wavefront, with the wavefront containing aberrations introduced by the eye. By determining the propagation direction of discrete portions (i.e., samples) of the wavefront, the aberrations introduced by the eye can be determined and corrected. In this type of system, increased accuracy in determining the aberrations can be achieved by reducing the size of the samples.

A general illustration of the generation of a wavefront is shown in FIG. 1. FIG. 1 is a schematic view of a wavefront 10 generated by reflecting a laser beam 12 off of the retina 14 of an eye 16. The laser beam 12 focuses to a small spot 18 on the retina 14. The retina 14, acting as a diffuse reflector, reflects the laser beam 12, resulting in the point source wavefront 10. Ideally, the wavefront 10 would be represented by a spherical or planar wavefront 20. However, aberrations introduced by the eye 16 as the wavefront 10 passes out of the eye 16 result in an imperfect wavefront, as illustrated by the wavefront 10. The wavefront 10 represents aberrations which lead to defocus, astigmatism, spherical aberrations, coma, and other irregularities. Measuring and correcting these aberrations allow the eye 16 to approach its full potential, i.e., the limits of visual resolution.

FIG. 2 is an illustration of a prior art apparatus for measuring the wavefront 10 as illustrated in FIG. 1. By measuring the aberrations, corrective lens can be produced and/or corrective procedures performed to improve vision. In FIG. 2, a laser 22 generates the laser beam 12 which is routed to the eye 16 by a beam splitter 24. The laser beam 12 forms a spot 18 on the retina 14 of the eye 16. The retina 14 reflects the light from the spot 18 to create a point source wavefront 10 which becomes aberrated as it passes through the lens and other components and material within the eye 16. The wavefront 10 then passes through the beam splitter 24 toward a wavefront sensor 26.

Typical prior art wavefront sensors 26 include either an aberroscope 28 and an imaging plane 30, as illustrated in FIG. 3, or a Hartman-Shack sensor 32 and an imaging plane 30, as illustrated in FIG. 4. The wavefront sensor 26 samples the wavefront 10 by passing the wavefront 10 through the aberroscope 28 or the Hartman-Shack sensor 32, resulting in the wavefront 10 producing an array of spots on the imaging plane 30. Each spot on the imaging plane 30 represents a portion of the wavefront 10, with smaller portions enabling the aberrations to be determined with greater accuracy. Generally, the imaging plane 30 is a charge coupled device (CCD) camera. By comparing the array of spots produced on the imaging plane 30 by the wavefront 10 with a reference array of spots corresponding to the wavefront of an ideal eye, the aberrations introduced by the eye 16 can be computed.

An example of a Hartman-Shack system described in U.S. Pat. No. 6,095,651 to Williams et al., entitled Method and Apparatus for Improving Vision and the Resolution of Retinal Images, filed on Jul. 2, 1999, is incorporated herein by reference.

The resolution of the aberrations in such prior art devices, however, is limited by the sub-aperture spacing 34 and the sub-aperture size 36 in an aberroscope 28 (see FIG. 3), and by the lenslet sub-aperture spacing 38, and focal length, in a Hartman-Shack sensor 32 (see FIG. 4). In addition, since each area is represented by a single spot, the amount of information captured for each area is limited. Also, because of foldover, reductions to sub-aperture spacing 34 and size 36 and lenslet sub-aperture spacing 38, the capabilities to obtain more detailed information are limited.

Foldover occurs in an aberroscope sensor 28, for example, when two or more spots 40A, 40B, and 40C on imaging plane 30 overlap, thereby leading to confusion between adjacent sub-aperture spots. Similarly, foldover occurs in Hartman-Shack sensors 32 when two or more spots 42A, 42B, 42C, and 42D on imaging plane 30 overlap. Foldover may result from a sub-aperture spacing 34, sub-aperture size 36, or lenslet spacing 38 which is too small; a high degree of aberration; or a combination of these conditions. Hence, the sub-aperture spacing 34 and sub-aperture size 36 in the aberroscope 28, and the lenslet sub-aperture spacing 38, and focal length in the Hartman-Shack sensor 32 must be selected to achieve good spatial resolution while enabling the measurement of large aberrations. Accordingly, the ability to measure a high degree of aberration comes at the expense of spatial resolution and/or dynamic range and vice versa.

The constraints imposed by the aberroscope and Hartman-Shack approaches limit the effectiveness of these systems for measuring aberrations with a high degree of accuracy. These limitations prevent optical systems from achieving their full potential. Accordingly, ophthalmic devices and methods which can measure aberrations with a high degree of accuracy would be useful.

SUMMARY OF THE INVENTION

The present invention provides for an apparatus and method for determining the aberrations of a wavefront with a high degree of accuracy. The apparatus includes a beam splitter for separating the wavefront into two components, mirror arrays for focusing each of the components to a plurality of discrete lines with the discrete lines of one component having a different orientation than the discrete lines of the other component, and an imaging device for detecting the discrete lines to determine wavefront aberrations. The method includes separating the wavefront into two components, focusing each of the components into a plurality of discrete lines with the discrete lines of one component having a different orientation than the discrete lines of the other component, and detecting information related to the discrete lines.

By generating discrete lines which represent the wavefront, the apparatus and method of the present invention are capable of measuring the wavefront with a high degree of accuracy. Since each of the plurality of discrete lines have a different orientation, the plurality of discrete lines essentially represent the wavefront as a grid. The present invention is able to provide more accurate information than prior art systems since the grid lines of the present invention provide more information for each section of the grid than the spots which would be generated by prior art systems to represent equivalent areas.

In a system for measuring the wavefront of an eye, the wavefront originates as a point source within the eye. The point source is generated by directing a beam of radiation (e.g., a laser) into the eye and scattering or reflecting the beam. A beam splitter disposed in the path of the laser beam directs the laser beam into the eye. The retina of the eye functions as a diffuse reflector for reflecting or scattering the beam. The wavefront resulting from the point source passes out of the eye and through the beam splitter to the wavefront sensor of the present invention. The wavefront sensor measures the aberrations of the wavefront introduced by the eye. Aberrations are then computed by a processor coupled to the wavefront sensor.

DETAILED DESCRIPTION OF THE INVENTION

Figure 1:
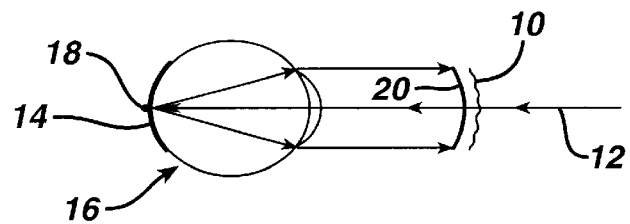
FIG. 1 is a schematic of a wave produced by a laser beam reflected by the retina of an eye.
Figure 2:
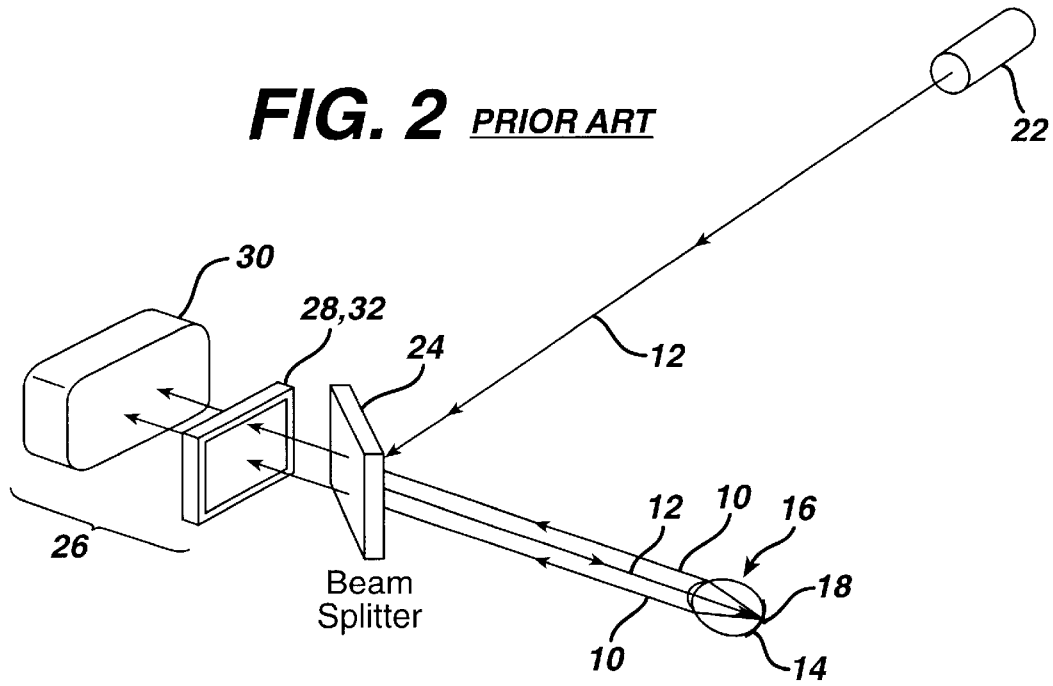
FIG. 2 is a schematic of a prior art apparatus for measuring aberrations introduced by an eye.
Figure 3:
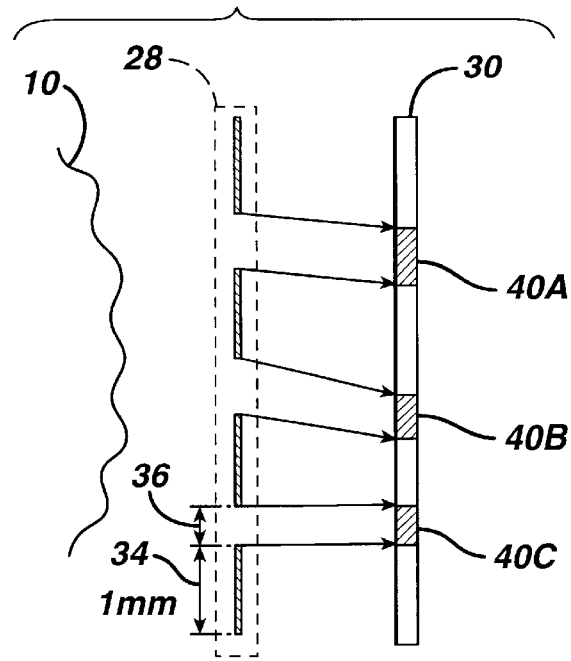
FIG. 3 is a schematic of an aberroscope for use in a prior art apparatus for measuring aberrations.
Figure 4:
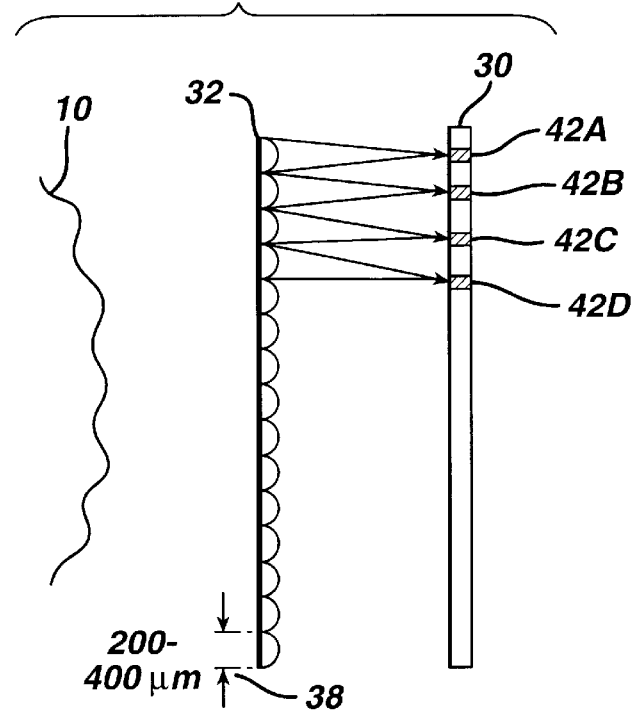
FIG. 4 is a schematic of a Hartman-Shack lenslet array for use in a prior art apparatus for measuring aberrations.
Figure 5:
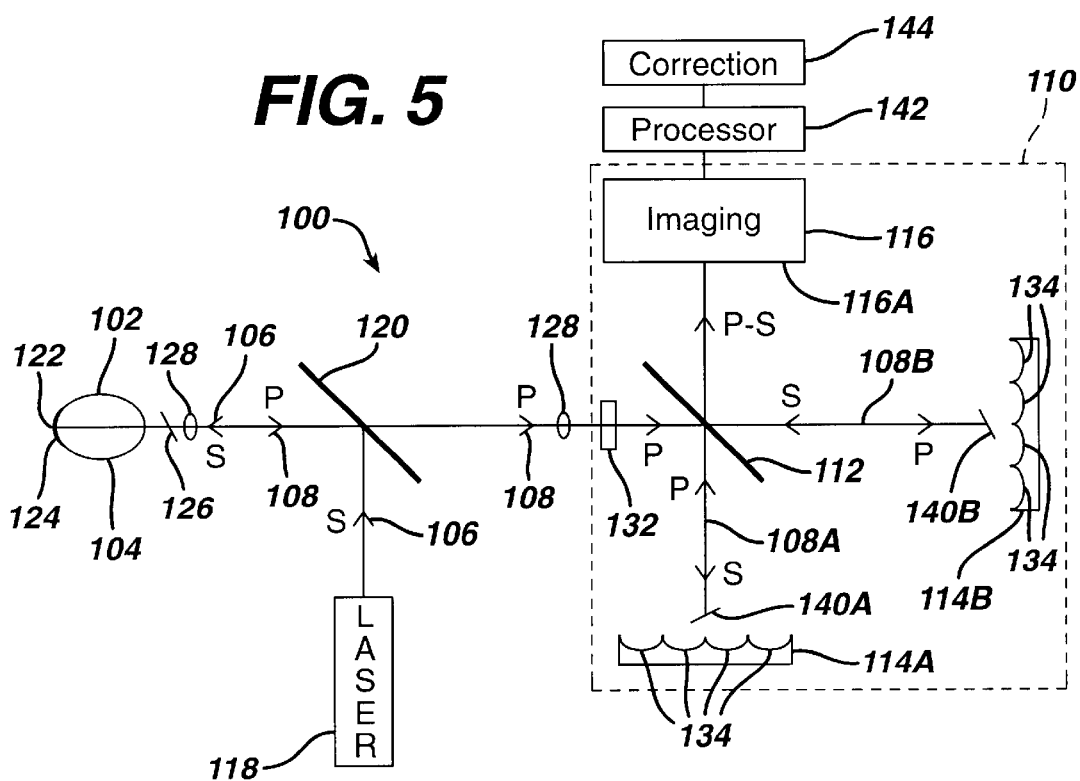
FIG. 5 is a schematic of an apparatus for measuring aberrations in a wavefront introduced by an optical system in accordance with the present invention.

Illustrated in FIG. 5 is a preferred embodiment of a wavefront measuring apparatus 100 in accordance with the present invention for measuring the aberrations of an optical system 102, which here is an eye 104. In a general overview, a beam 106 is generated and directed into the eye 104. The beam 106 is reflected as a wavefront 108 which passes out of the eye 104 and is then directed toward a wavefront detection (WD) device 110 for detecting aberrations within the wavefront 108. In the WD device 110, the wavefront 108 is passed toward a WD beam splitter 112 where the wavefront 108 is separated into two components. One of the wavefront components is reflected toward a first mirror array 114A and the other component is passed through the beam splitter 114 toward a second mirror array 114B. The mirror arrays 114A,114B divide, reflect, and focus the wavefront component incident on their respective surfaces to a plurality of discrete lines which are ultimately detected by an imaging device 116. Other components within the WD device 110 are used for routing the two wavefront components. The present invention is now described in more detail.

In the preferred embodiment, and for purposes of illustration, a radiation source 118 generates the beam 106, and a wavefront generation (WG) beam splitter 120 directs the beam 106 toward the eye 104, and thereafter directs the resultant wavefront 108 out of the eye 104 toward the WD device 110. In the preferred embodiment, the wavefront 108 is linearly polarized. Alternatively, the wavefront 108 may be unpolarized or circularly polarized.

The illustrated optical system 102 is the eye 104. Alternatively, the optical system 102 may include a reflective surface and a contact lens or eyeglass, an eye and a contact lens or eyeglass, a telescope, a microscope, or other type of optical system to be analyzed. In the illustrated embodiment, the beam 106 from the radiation source 108 focuses to a spot 122 on the retina 124 of the eye 104. A focusing lens or system of lenses may be used in the path of the beam 106 to account for defocus and/or astigmatism of the eye 104. The retina 124, acting as a diffuse reflector, effectively becomes the source for light leaving the eye 104, thereby creating the wavefront 108. Aberrations due to imperfections within the eye 104 affect the wavefront 108.

The radiation source 110 is a device capable of generating a focused beam of photons, and is preferably a laser. Alternative radiation sources 110 include a laser diode, super-luminescent diode, or essentially any radiation device capable of generating a focused beam as may be known in the art. Additionally, the radiation source 110 may include a spatial filter for correcting noise associated with the radiation source 110. In the preferred embodiment, the beam 106 generated by the radiation source 110 is polarized.

The WG beam splitter 120 is capable of selectively passing and directing beams. Here, the WG beam splitter 120 is configured to reflect the beam 106 toward the optical system 102 and to pass the wavefront 108 projecting from the optical system 102 toward the WD device 110 unaltered. In the preferred embodiment, the WG beam splitter 120 is a polarizing beam splitter which passes light polarized in one direction and reflects light polarized in the other direction. A common naming convention is to refer to light polarized in one direction as "p"-polarized light and light polarized at a 90 degree angle to the "p"-polarized light as "s"-polarized light. Once the WG beam splitter 120 is aligned, the axis which passes the "p"-polarized light is called the "p" axis. The details which enable the WG beam splitter 120 to direct light appropriately for use in the preferred embodiment are discussed below.

The quarter-wave plate 126 is an optical component which assists systems 100 of the type illustrated here, i.e. systems which use polarization for routing beams, to distinguish between beams entering the eye 104 and those leaving the eye 104. Prior to reaching the plate 126, the beam 106 is linearly polarized (e.g., in an "s" direction). After passing through the plate 126, the beam 106 is circularly polarized in one direction. The circularly polarized beam 106 is focused to a spot 122 on the retina 124 of the eye 104. The wavefront 108 is produced by reflecting the circularly polarized beam 106 off of the retina 124. It is understood by those skilled in the art that the wavefront 108 will be circularly polarized in a direction opposite to that of the beam 106 due to reflection by the retina 124. After the wavefront 108 emanates from the eye 104, the quarter-wave plate 126 will linearly polarize the circularly polarized wavefront 108 to produce a linearly polarized wavefront 108 (e.g., in a "p" direction) having an orientation that is 90 degrees different from the linear polarization of the beam 106 which entered the eye 104.

In an illustrative example, the WG beam splitter 120 reflects a linearly "s"-polarized beam 106 (i.e., polarized at a 90 degree angle to the p-axis of the WG beam, splitter 120) toward the eye 104. The linearly polarized wavefront 108 which exits the eye 104 is "p"-polarized (i.e., polarized on axis with the p-axis of the WG beam splitter 120) due to the quarter-wave plate 126 and reflection within the eye 104. Since the polarization of the wavefront 108 is on axis with the p-axis of the WG beam splitter 120, the WG beam splitter 120 will allow the wavefront 108 to pass unaltered toward the WD device 110.

One or more optical devices, such as lenses 128, are positioned within the wavefront measurement apparatus 100 to direct the wavefront 108 between the eye 104 and the wavefront detection device 110. They preserve the propagation directions of the waves which make up the wavefront 108 as they are passed from the eye 104 to the WD device 110. Such devices are well known in the art.

In the preferred embodiment, the wavefront detection (WD) device 110 includes a WD beam splitter 112, two mirror arrays 114A, B, two quarter-wave plates 130A, B, a half-wave plate 132, and an imaging device 116. The WD beam splitter 112 separates an incoming wavefront 108 into two components 108A and 108B with each of the components representative of the entire wavefront 108. The WD beam splitter 112 reflects approximately half the intensity of the wavefront 108 as the wavefront 108A (e.g., as light polarized in an "s" direction) toward the mirror array 114A, and will pass the other half of the intensity of the wavefront 108 as the wavefront 108B (e.g., as light polarized in a "p" direction) toward the mirror array 114B.

It is understood by those skilled in the art that light polarized in a given direction can be broken down into two components by orienting the axis of a polarized beam splitter and the polarization axis of the polarized light at a 45 degree angle relative to one another. In this orientation, the polarized beam splitter will reflect half of the intensity of the polarized light and transmit half of the intensity of the polarized light. For example, the wavefront 108 can be broken down into two polarized components (e.g., "s" and "p" polarized light) by orienting the axis of the WD beam splitter 112 and the polarization of the wavefront 108 relative to one another such that the WD beam splitter 112 reflects "s"-polarized light as the wavefront 108A and passes "p"-polarized light as the wavefront 108B.

In order to orient the axis of the WD beam splitter 112 and the polarization of the wavefront 108 at a 45 degree angle relative to one another, the polarization of the wavefront 108 can be rotated relative to the axis of the WD beam splitter 112 and/or the axis of the WD beam splitter 112 can be rotated relative to the polarization of the wavefront 108. In the preferred embodiment, a known half-wave plate 132 is used to change the polarization axis of the wavefront 108 by 45 degrees to obtain "p*"-polarized light. If the axis of the WD beam splitter 112 is aligned to pass "p"-polarized light and to reflect "s" polarized light, the "p*"-polarized light can be divided into two components (e.g., "s" and "p") since the "p*"-polarized wavefront 108 is oriented at a 45 degree angle to the "p" polarization axis of the WD beam splitter 112. In an alternative embodiment, the axis of the WD beam splitter is rotated by 45 degrees, along with the other components within the WD device 110, relative to the wavefront 108, thereby removing the need for the half-wave plate 132. In this arrangement, the WD beam splitter 112 will pass a portion of the intensity of the "p" polarized light as "p*" polarized light and reflect the remaining intensity of the "p" polarized light as "s*" polarized light.

In addition, it will be understood that if the wavefront 108 is made up of circularly polarized light or unpolarized light, the orientation of the WD beam splitter 112 will be irrelevant as circularly polarized light and unpolarized light can each be conceptually broken into two components regardless of the orientation of the axis of the WD beam splitter 112. The circularly polarized light and the unpolarized light can each be broken down into two components regardless of the orientation of the WD beam splitter 112 because they each contain an equal distribution of light which allows them to be split into two equal components at right angles to one another. Therefore, for circularly polarized light or unpolarized light, the WD beam splitter 112 will reflect half the light as "s"-polarized light toward the mirror array 114A and pass half the light as "p"-polarized light toward the mirror array 114B regardless of the orientation of the WD beam splitter 112 and without the use of a half-wave plate 132.

With further reference to FIG. 5, the mirror arrays 114A, B divide, reflect, and focus light incident on their surfaces to a plurality of discrete lines. Each of the mirror arrays 114A, B are made up of a plurality of cylindrical mirrors 134, with each of the cylindrical mirrors 134 corresponding to a rectangular portion of the wavefront 108. Preferably, the cylindrical mirrors 134 are formed of a plurality of reflective parallel grooves. The mirror arrays 114A, B are oriented relative to one another such that the rectangular portions and the discrete lines produced from the rectangular portions by one mirror array 114A are distinguishable from the rectangular portions and the discrete lines produced from the rectangular portions by the other mirror array 114B.

Figure 6:
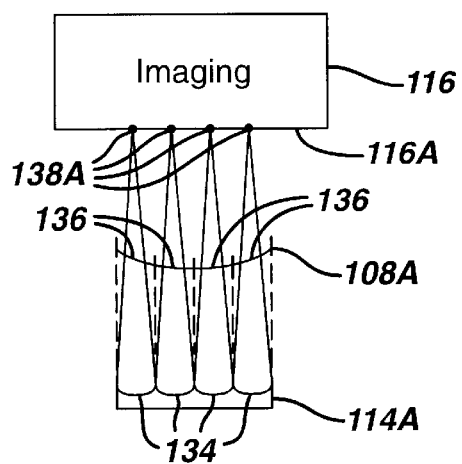
FIG. 6 is an illustrative schematic of a mirror array reflecting and focusing a wavefront for use in the apparatus of FIG. 5 in accordance with the present invention.

FIG. 6 illustrates the operation of one of the mirror arrays 114A, with the other mirror array 114B operating in a similar manner. For a wavefront 108A traveling toward the mirror array 114A, the cylindrical mirrors 134 will divide the wavefront 108A which is incident on their respective surfaces into wavefront portions 136. The cylindrical mirror array 114A reflects the wavefront portions 136 and focus them to a plurality of discrete lines 138A (represented by spots on imaging device 116). Preferably, the cylindrical mirror array 114A focuses the plurality of discrete lines on an imaging surface 116A (represented by the bottom edge of the imaging device 116).

Figure 6A:
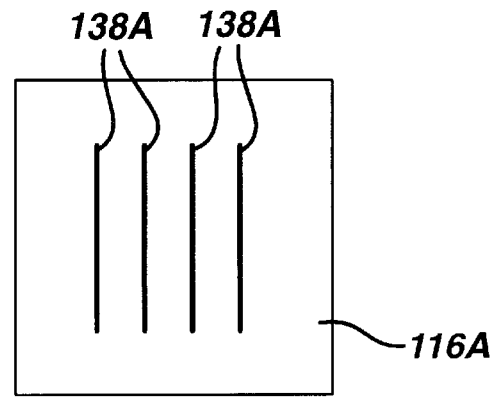
FIG. 6A is a schematic illustrating a plurality of discrete lines of one orientation displayed on an imaging surface resulting from one mirror array of FIG. 5.
Figure 6B:
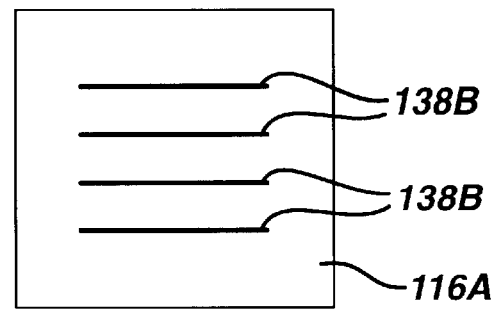
FIG. 6B is a schematic illustrating a plurality of discrete lines of another orientation displayed on an imaging surface resulting from the other mirror array of FIG. 5.
Figure 6C:
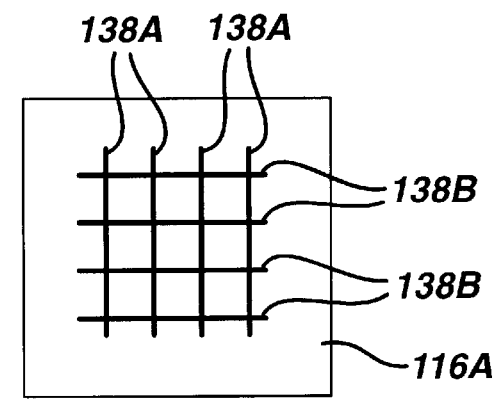
FIG. 6C is a schematic illustrating the combination of the plurality of discrete lines of FIG. 6A with the plurality of discrete lines of FIG. 6B.

In the preferred embodiment, illustrated in FIGS. 6A and 6B, the mirror arrays 114A, B are oriented such that one of the mirror arrays 114A divides the wavefront 108A into a plurality of vertical rectangular portion which are reflected and focused to a plurality of vertical discrete lines 138A (FIG. 6A) on the imaging surface 116A, and the other mirror array 114B divides the wavefront 108B into a plurality of horizontal rectangular portions which are reflected and focused to a plurality of horizontal vertical lines 138B (FIG. 6B) on the imaging surface 116A. Preferably, the light which generates the discrete lines 138A, B is directed towards the imaging surface 116A by the WD beam splitter 112, discussed in detail below. In the preferred embodiment, the plurality of discrete vertical lines 138A and the plurality of discrete horizontal lines 138B are focused onto the same imaging surface 116A to form a grid which is representative of the wavefront 108, as illustrated in FIG. 6C. In an alternative embodiment, each of the plurality of discrete lines may be focused to a different imaging device.

The imaging device 116 (FIG. 5) is capable of precisely detecting the location of energy incident to an imaging plane 116A. Preferably, the imaging device 116 is a charge coupled device (CCD) camera which is capable of converting energy incident to an imaging plane into a digital representation. Charge coupled devices are well known and a suitable device for use with the present invention would be readily apparent to those skilled in the art.

The aberrations which are introduced by the optical system 102 affect the discrete lines 138A, B. For an aberration free optical system 102, the discrete lines 138A, B would be substantially straight. Aberrations within the optical system 102, however, cause the discrete lines 138A, B to deviate from being substantially straight. The aberrations of the optical system 102 can be determined by measuring the difference in location between individual points on a discrete line 138A, 138B produced from an optical system 102 and corresponding points on the substantially straight discrete line 138A, 138B for an aberration free optical system 102, and calculating the aberration which would produce the measured difference for each point. The determined aberrations for the individual points are then combined to determine the aberrations of the optical system 102.

Methods for calculating aberrations based on the difference between discrete lines 138A, B produced by the optical system 102 and the substantially straight discrete lines 138A, B produced by an aberration free system 102 will be readily apparent to those in the art. The discrete lines 138A, B used to represent the wavefront 108 allow the wavefront 108 to be analyzed in greater detail than in prior art systems which generate a finite number of spots to represent the wavefront 108, because more reference locations are available for performing calculations.

The quarter-wave plates 140A, B modify their respective wavefront components 108A, B as described below so that they can be recombined at the WD beam splitter 112 for measurement by a single imaging device 116. With reference to FIG. 5, a polarized WD beam splitter 112 is used for purposes of the present illustration. As previously explained, the wavefront 108 coming from the eye 104 is split into component waves 108A and 108B by the WD beam splitter 112, the wavefront component 108A being polarized in the "s" direction and thus reflecting downward toward the mirror array 114A, the wavefront component 108B being polarized in the "p" direction and thus passing through the WD beam splitter 112 toward the mirror array 114B. After reflecting from the WD beam splitter 112, the wavefront component 108A passes through the quarter-wave plate 140A which changes the "p" linearly polarized wavefront component 108A to a circularly polarized wavefront 108A. When the circularly polarized wavefront 108A is reflected by the mirror array 114A, the circular polarization is reversed. Upon passing back through the quarter-wave plate 140A, towards the WD beam splitter 112, the reversed circularly polarized wavefront 108A will be changed to a linearly polarized wavefront component 108A in the "p" direction, as opposed to the "s" direction, due to the reversed circular polarization. Being now linearly polarized in the "p" direction, the wavefront component 108A will pass through the beam splitter 112 towards the imaging device 116.

In a similar manner, the "p" linearly polarized wavefront component 108B passing through the WD beam splitter 112 towards the mirror array 114B passes through the quarter-wave plate 140B which changes the "p" linearly polarized wavefront component 108B to a circularly polarized wavefront 126B. The reflection of this wavefront 108B by the mirror array 114B then reverses the circular polarization, and, upon passing back through the quarter-wave plate 140B towards the WD beam splitter 112 is changed to an "s" linearly polarized wavefront component 108B which is now reflected by the WD beam splitter 112 toward the imaging plane 116, and thereby recombined with the wavefront component 108A.

In an alternative embodiment (not shown), multiple imaging devices 116 can be used, thereby removing the need to recombine the wavefront components 108A, 108B. Therefore, according to this embodiment, the quarter-wave plates may be eliminated without departing from the spirit and scope of the present invention.

The processor 142 receives information from the imaging device 116 and analyzes the information to compute the aberrations. The information may be stored in a storage register prior to processing by processor 142 or may be processed immediately. It is apparent to those skilled in the art that the receipt of information from the imaging device 116 and the processing of information may be performed by a single processor or divided among a plurality of processors.

In accordance with an embodiment of the present invention, an aberration correction device 144 is coupled to the processor 142. Alternatively, information calculated by the processor 142 may be stored on a hard drive, diskette, server, compact disc, digital versatile disc, or essentially any device capable of storing information. The stored information is then passed to an aberration correction device 144. The aberration correction device 144 includes a known lens grinder, contact lens manufacturing system, surgical laser system, or other optical system correction device. In a surgical laser system, a laser can be optically positioned relative to the WG beam splitter 120 to direct a laser cutting beam toward the cornea of the eye 104, in a manner well known in the art, for the purpose of performing ophthalmic surgery.

For illustrative purposes, the present invention has been described in terms of measuring wavefront aberrations introduced by a human eye. However, it will be readily apparent to those skilled in the art that the present invention can be used to measure aberrations created by other optical systems, e.g. eyeglasses, telescopes, binoculars, monoculars, contact lenses, non-human eyes, or combination of these systems.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A sensor for detecting aberrations of a wavefront emitted from an optical system, said sensor comprising:

a beam splitter for receiving the wavefront and separating the wavefront into a first component having a first polarization and a second component having a second polarization, said first polarization being distinguishable from said second polarization;

a first mirror array reflecting and focusing said first component to a first plurality of discrete lines having a first orientation;

a second mirror array for reflecting and focusing said second component to a second plurality of discrete lines having a second orientation different from said first orientation; and an imaging device for detecting said first plurality of discrete lines and said second plurality of discrete lines.

2. The sensor in accordance with claim 1, wherein said first mirror array and said second mirror array are configured to orient said first plurality of discrete lines substantially perpendicular to said second plurality of discrete lines.

3. The sensor in accordance with claim 2, wherein said imaging device is a charge coupled device (CCD).

4. The sensor in accordance with claim 3, further comprising a processor for analyzing said first and second pluralities of discrete lines produced on said CCD.

5. The sensor in accordance with claim 1, further comprising:

a first quarter-wave plate optically positioned between said beam splitter and said first mirror array to convert said first component from linear polarization of a first propagation direction to circular polarization upon the passing of said first component through said first quarter-wave plate to said first mirror array and to convert said first component from circular polarization to linear polarization of a second propagation direction upon the passing of said first component through said first quarter-wave plate from said first mirror array; and a second quarter-wave plate optically positioned between said beam splitter and said second mirror array to convert said second component from linear polarization of a third propagation direction to circular polarization upon the passing of said second component through said second quarter-wave plate to said second mirror array and to convert said second component from circular polarization to linear polarization of a fourth propagation direction upon the passing of said second component through said second quarter-wave plate from said second mirror array.

6. The sensor in accordance with claim 5, wherein said beam splitter is configured to combine said first and second components after reflection by said first and second mirror arrays, respectively.

7. The sensor in accordance with claim 6, wherein said beam splitter is a polarizing beam splitter configured to pass said first component linearly polarized in said first propagation direction and said second component linearly polarized in said fourth propagation direction, and to reflect said first component linearly polarized in said second propagation direction and said second component linearly polarized in said third propagation direction.

8. The sensor in accordance with claim 7, wherein said first propagation direction and said fourth propagation direction are the same, and said second propagation direction and said third propagation direction are the same.

9. The sensor in accordance with claim 1, wherein said imaging device comprises a single imaging device for detecting both said first plurality of discrete lines and said second plurality of discrete lines.

10. An apparatus for measuring aberrations of a wavefront emitted from an optical system, comprising:

a beam splitter for receiving and separating the wavefront into a first component having a first polarization and a second component having a second polarization, said first polarization being distinguishable from said second polarization;

a first mirror array for reflecting and focusing said first component to a first plurality of discrete lines having a first orientation;

a second mirror array for reflecting and focusing said second component to a second plurality of discrete lines having a second orientation different from said first orientation; and an imaging device for detecting information related to said first plurality of discrete lines and said second plurality of discrete lines; and a processor for computing wavefront aberrations from the detected information received from said imaging device.

11. The apparatus in accordance with claim 10, further comprising:

a radiation source for generating a beam to be directed to the optical system to produce the wavefront.

12. The apparatus in accordance with claim 10, further comprising:

a first quarter-wave plate positioned between said beam splitter and said first mirror array to convert said first component from linear polarization to circular polarization upon the passing of said first component through said first quarter-wave plate to said first mirror array and to convert said first component from circular polarization to linear polarization upon the passing of said first component through said first quarter-wave plate from said first mirror array; and a second quarter-wave plate positioned between said beam splitter and said second mirror array to convert said second component from linear polarization to circular polarization upon the passing of said second component through said second quarter-wave plate to said second mirror array and to convert said second component from circular polarization to linear polarization upon the passing of said second component through said second quarter-wave plate from said second mirror array.

13. The apparatus in accordance with claim 10, wherein the wavefront is linearly polarized.

14. The apparatus in accordance with claim 13, further comprising:

a half-wave plate positioned between the wavefront and said beam splitter for altering the linear polarization axis of the wavefront.

15. The apparatus in accordance with claim 10, wherein the wavefront is non-polarized.

16. The apparatus in accordance with claim 10, wherein the wavefront is circularly polarized.

17. A method for measuring a wavefront emitted from an eye comprising the steps of:

(a) separating the wavefront into a first component and a second component;

(b) focusing said first component to a first series of discrete lines having a first orientation, and focusing said second component to a second series of discrete lines having a second orientation, said second orientation being different from said first orientation; and (c) detecting information related to said first series of discrete lines and said second series of discrete lines for determining the aberrations of the wavefront.

18. The method in accordance with claim 17, wherein step (a) comprises separating the wavefront into two polarized wavefronts having different polarizations.

19. The method in accordance with claim 18, wherein said focusing step comprises focusing one of said polarized wavefronts into said first series of discrete lines and focusing the other one of said polarized wavefronts into said second series of discrete Lines, said discrete lines for one of said polarized wavefronts being substantially perpendicular to said discrete lines of the other.

20. The method in accordance with claim 19, wherein step (b) further comprises combining said first component and said second component.

21. The method of claim 20, wherein said separating and combining steps are performed by a beam splitter.

22. The method of claim 21:
   wherein said separating step separates the wavefront into a first intermediate wavefront having a first linear polarization to generate said first component and a second intermediate wavefront having a second linear polarization different from said first linear polarization to generate said second component;
   further comprising the step of, (a1) converting said first linear polarization to a first circular polarization and said second linear polarization to a second circular polarization between said separating step (a) and said focusing step (b);
   wherein step (b) further comprises the step of reflecting said first component and said second component, said reflecting step converting said first circular polarization to a third circular polarization of an opposite direction than said first circular polarization and converting said second circular polarization to a fourth circular polarization of an opposite direction than said second circular polarization;
   further comprising the step of, (b1) converting said third circular polarization to a third linear polarization and converting said fourth circular polarization to a fourth linear polarization between said reflecting and combining of step (b), wherein said third linear polarization is substantially the same as said second linear polarization and said fourth linear polarization is substantially the same as said first linear polarization; and
   wherein said combining step comprises combining said first component having said third linear polarization with said second component having said fourth linear polarization.

23. The method in accordance with claim 17, further comprising the step of:
   analyzing the detected information to determine the wavefront aberrations.

24. The method in accordance with claim 23, wherein said analyzing step comprises:
   comparing information obtained during said detecting step with known values for an aberration free wavefront; and
   calculating the aberration of the wavefront.

* * * * *